(12) United States Patent
Sugaya et al.

(10) Patent No.: US 8,744,040 B2
(45) Date of Patent: Jun. 3, 2014

(54) X-RAY CT APPARATUS AND METHOD

(75) Inventors: Yoshiaki Sugaya, Tokyo (JP); Taiga Goto, Tokyo (JP); Koichi Hirokawa, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 302 days.

(21) Appl. No.: 13/144,326

(22) PCT Filed: Jan. 21, 2010

(86) PCT No.: PCT/JP2010/050703
§ 371 (c)(1),
(2), (4) Date: Jul. 13, 2011

(87) PCT Pub. No.: WO2010/087267
PCT Pub. Date: Aug. 5, 2010

(65) Prior Publication Data
US 2011/0274240 A1 Nov. 10, 2011

(30) Foreign Application Priority Data
Feb. 2, 2009 (JP) ................................. 2009-021203

(51) Int. Cl.
*A61B 6/03* (2006.01)
(52) U.S. Cl.
USPC .............................................. 378/16; 378/4
(58) Field of Classification Search
USPC ........................................................ 378/16
See application file for complete search history.

(56) References Cited

U.S. PATENT DOCUMENTS

2005/0089137 A1* 4/2005 Toth et al. ....................... 378/19

FOREIGN PATENT DOCUMENTS

| JP | 2000-51194   | 2/2000 |
| JP | 2006-75339   | 3/2006 |
| JP | 2007-185358  | 7/2007 |
| JP | 2007-190415  | 8/2007 |
| JP | 2008-18044   | 1/2008 |

OTHER PUBLICATIONS

International Search Report in PCT/JP2010/050703, May 8, 2010.

* cited by examiner

*Primary Examiner* — Hoon Song
*Assistant Examiner* — Danielle Fox
(74) *Attorney, Agent, or Firm* — Cooper & Dunham LLP

(57) ABSTRACT

An X-ray CT apparatus includes: an X-ray source which emits X-rays while rotating around a subject; a compensation filter which adjusts at least one of the output distribution and the spectral distribution of the X-rays emitted from the X-ray source to the subject; an X-ray detector which is disposed opposite to the X-ray source with the subject interposed therebetween, rotates together with the X-ray source, and detects the amount of X-rays transmitted through the compensation filter and the subject; an image operation unit which reconstructs a tomographic image of the subject on the basis of the detected amount of X-rays; a display unit which displays the tomographic image; a control unit which controls each of the constituent components; and a compensation unit which compensates for deterioration of image quality, which is based on the amount of displacement between the rotation center of the X-ray source and a desired position of the subject, by changing an X-ray tube current modulation pattern indicating a time-series change of emission of the X-rays and/or by moving the position of the subject.

15 Claims, 15 Drawing Sheets

F I G . 1
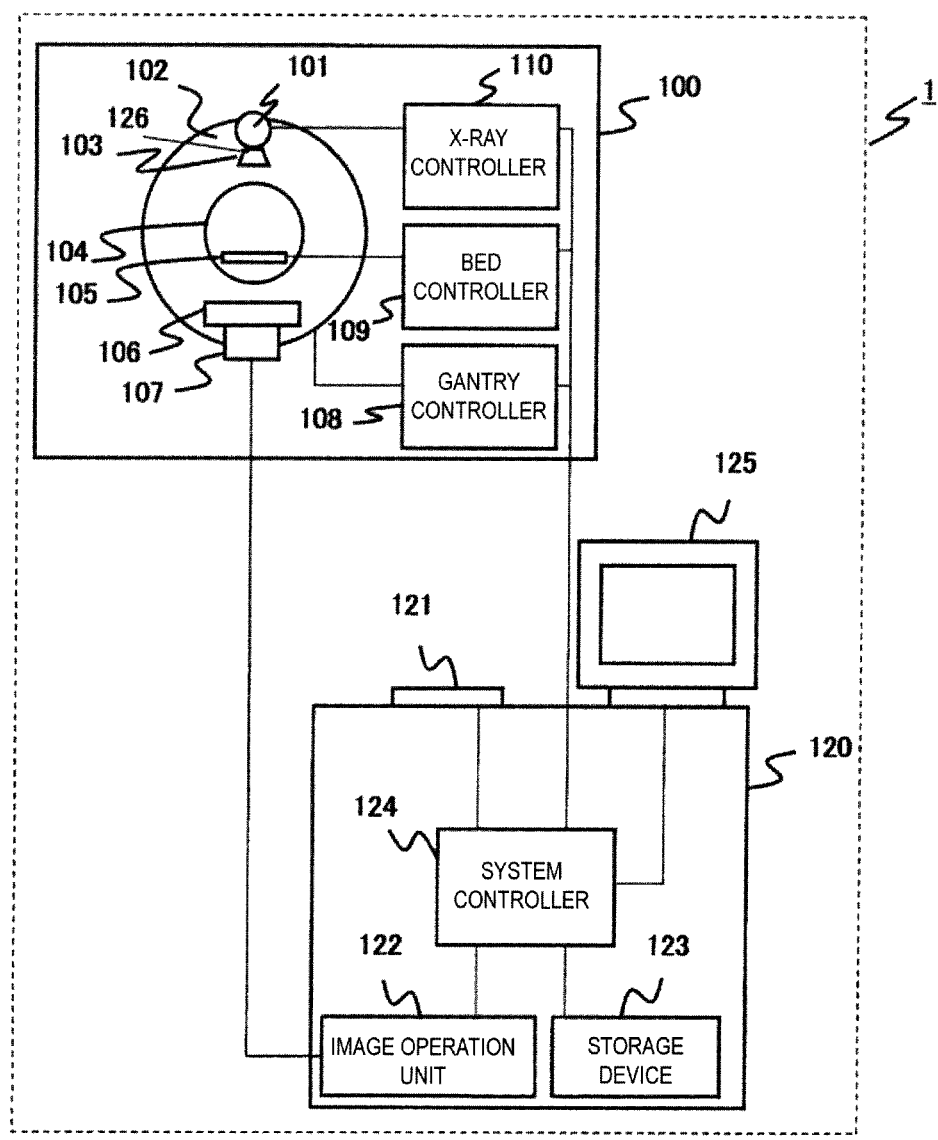

(a)        (b)

FIG. 5
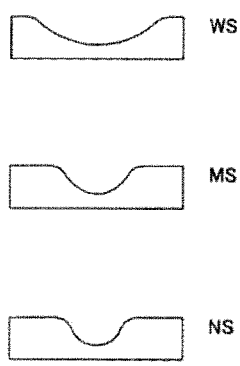
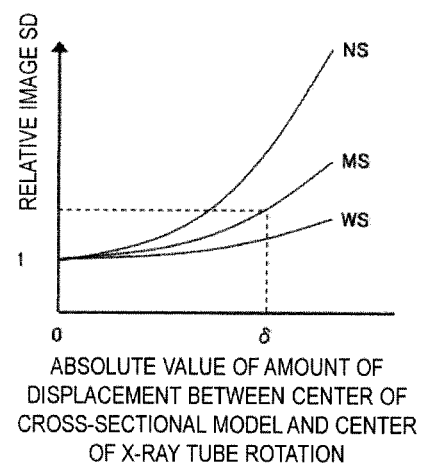
(a)                    (b)

FIG. 6
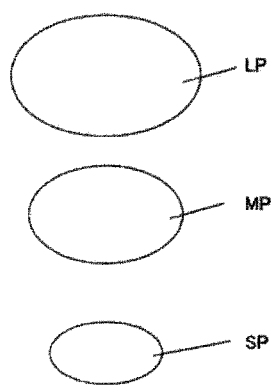
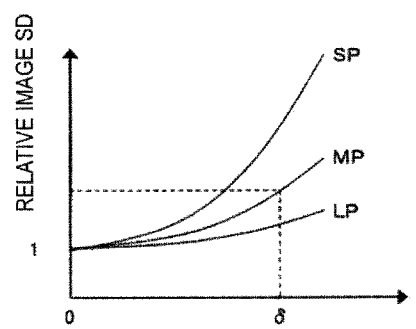
ABSOLUTE VALUE OF AMOUNT OF
DEVIATION BETWEEN CENTER OF
CROSS-SECTIONAL MODEL AND CENTRE
OF X-RAY TUBE ROTATION
(a)                    (b)

F I G . 1 2
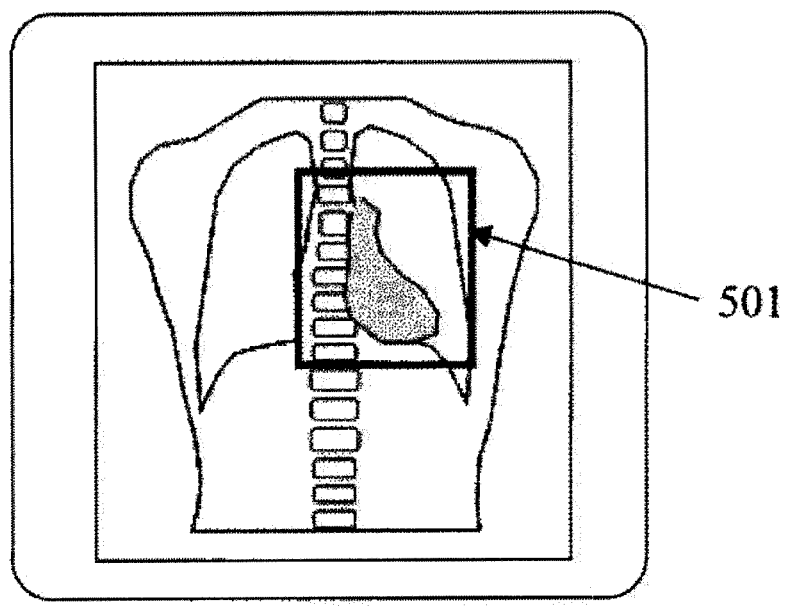

(a)  (b)

F I G. 1 5
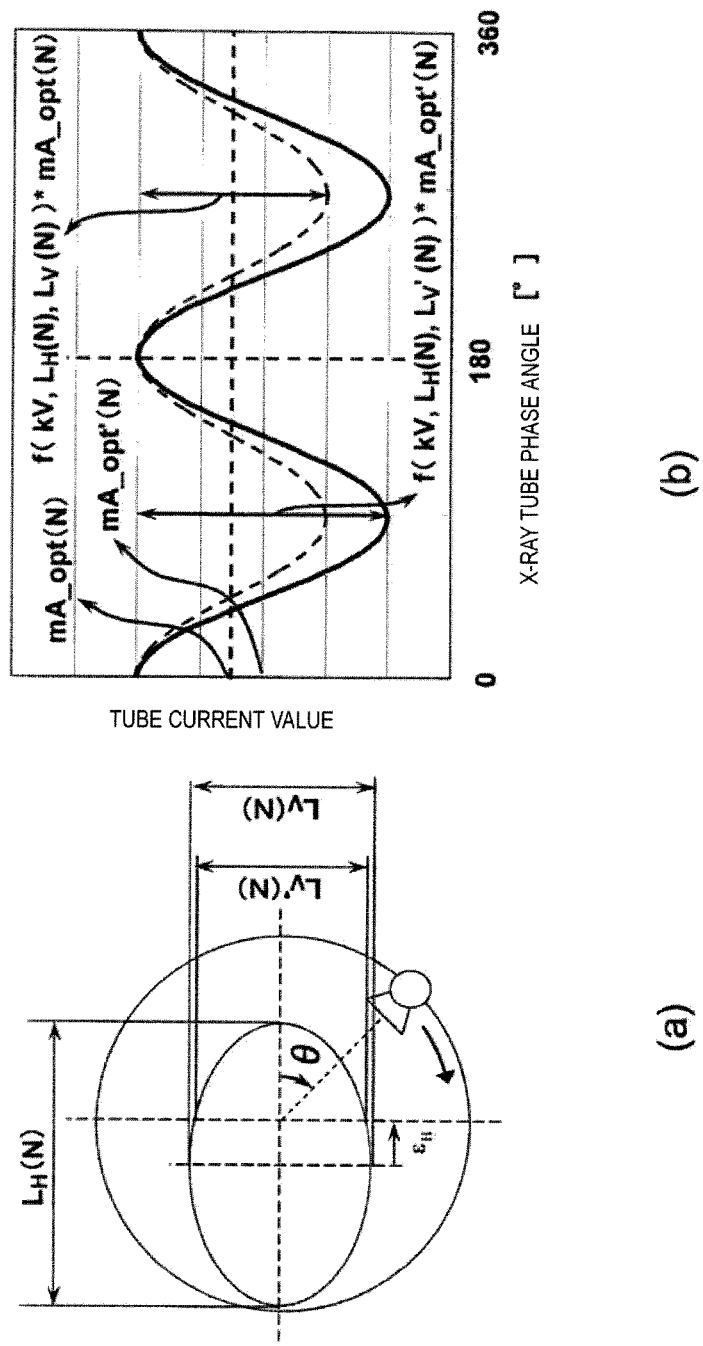

X-RAY CT APPARATUS AND METHOD

TECHNICAL FIELD

The present invention relates to an X-ray CT apparatus which controls an X-ray tube current during scanning to suppress the exposure amount of a subject and in particular, to an X-ray CT apparatus capable of appropriately setting the subject position or a change pattern of the tube current during scanning according to the positioning of a compensation filter and the subject.

BACKGROUND ART

The X-ray CT apparatus is an apparatus which emits X-rays as fan beams or cone beams (conical or pyramid shaped beams) to the subject, acquires projection data which is the information regarding the intensity of the X-rays transmitted through the subject, and forms the distribution information of an X-ray absorption coefficient inside the subject as an image on the basis of the projection data.

When the X-ray tube current is constant as a scanning condition of the X-ray CT apparatus, the amount of X-rays may be excessive or deficient depending on the emission angle or an emitted portion of X-rays. In this regard, an X-ray CT apparatus having a tube current automatic control function (CT-AEC (Automatic Exposure Control; the same hereinbelow)) of calculating an elliptical cross-sectional model of the subject from the scanogram projection data and calculating the X-ray tube current value from the area and the aspect ratio of the elliptical cross section is known as a technique in the related art (for example, refer to PTL 1). Using this technique, the amount of X-rays can be optimally controlled so that the target image quality set in advance can be realized. Accordingly, it is possible to maintain the almost constant image quality irrespective of an emitted portion.

On the other hand, the subject has a shape in which the thickness at the body axis center is large and the periphery is thin. Accordingly, X-rays emitted from the X-ray tube are transmitted through a Bow-tie filter (generally, called a Bow-tie filter or a compensation filter; hereinafter, called a compensation filter) in which the thickness at the center (position on a line connecting a focal point of X-rays generated by an X-ray tube and the gantry center) is small and the thickness of the periphery is large. As a result, the intensity of X-rays transmitted through the subject is adjusted so as to be almost constant in a body width direction. That is, by emitting X-rays transmitted through the thinnest portion of the compensation filter to the center of the subject having an almost elliptical cross section, the intensity of X-rays transmitted through the subject is adjusted so as to be almost constant in the body width direction.

CITATION LIST

Patent Literature

[PTL 1] JP-A-2001-043993
[PTL 2] JP-A-2006-075339
[PTL 3] JP-A-2003-033346

SUMMARY OF INVENTION

Technical Problem

In the related art, however, the subject may not necessarily be disposed at the gantry center of the X-ray CT apparatus. In this case, there is a problem in that the subject center is not disposed on the line connecting the focal point of the X-ray tube and the center of the compensation filter (or the rotation center of an X-ray source). Then, since the amount of X-rays emitted to the subject center is reduced, a problem occurs in which the image quality of a central portion of the subject deteriorates. This means that a case occurs in which the target image quality set in advance cannot be realized when using the above CT-AEC. This is not preferable in practical use.

PTL 2 discloses a technique of solving the positional displacement of the subject by moving a compensation filter. However, it is technically difficult to provide high-speed moving means for such a compensation filter in recent X-ray CT apparatuses with an extremely high scan speed. Even if possible, problems of noise or high cost can be easily expected.

It is an object of the present invention to provide an X-ray CT apparatus capable of acquiring a high-quality CT image even if there is a positional displacement between a subject and a compensation filter.

Solution to Problem

In order to solve the above-described problems, the present invention is characterized in that an X-ray CT apparatus includes: an X-ray source which emits X-rays while rotating around a subject; a compensation filter which adjusts at least one of output distribution and spectral distribution of the X-rays emitted from the X-ray source to the subject; an X-ray detector which is disposed opposite to the X-ray source with the subject interposed therebetween, rotates together with the X-ray source, and detects the amount of X-rays transmitted through the compensation filter and the subject; an image operation unit which reconstructs a tomographic image of the subject on the basis of the detected amount of X-rays; a display unit which displays the tomographic image; a control unit which controls each of the constituent components; and a compensation unit which compensates for deterioration of image quality, which is based on the amount of displacement between the rotation center of the X-ray source and a desired position of the subject, by changing an X-ray tube current modulation pattern indicating a time-series change of emission of the X-rays and/or by moving the position of the subject.

In addition, the present invention is characterized in that an X-ray CT method includes: (1) a step of emitting X-rays from an X-ray source while rotating the X-ray source around a subject; (2) a step of detecting the amount of X-rays transmitted through a compensation filter, which adjusts at least one of output distribution and spectral distribution of the X-rays emitted from the X-ray source to the subject, and the subject by means of an X-ray detector which is disposed opposite to the X-ray source with the subject interposed therebetween and rotates together with the X-ray source; (3) a step of reconstructing a tomographic image of the subject on the basis of the detected amount of X-rays by means of an image operation unit; (4) a step of displaying the tomographic image; and (5) a step of compensating for deterioration of image quality, which is based on the amount of displacement between the rotation center of the X-ray source and a desired position of the subject, by changing an X-ray tube current modulation pattern indicating a time-series change of emission of the X-rays and/or by moving the position of the subject.

Advantageous Effects of Invention

The present invention can provide an X-ray CT apparatus capable of acquiring a high-quality CT image by appropriately setting the bed position or a change pattern of the tube current during scanning according to the positional displacement between the subject and a compensation filter.

BRIEF DESCRIPTION OF THE DRAWINGS

FIG. 1 is an explanatory view of an apparatus to which the present invention is applied.

FIG. 5 is a view showing the relationship between the amount of displacement between the same cross-sectional model center and the center of X-ray tube rotation and a relative image SD of each compensation filter shape.

FIG. 6 is a view showing the relationship between the amount of displacement between the center of X-ray tube rotation and the cross-sectional model center when cross-sectional models are different and a relative image SD.

FIG. 12 is an example of a display screen when a scan region on a scanogram is limited.

FIG. 15 is an outline of a scan tube current modulation curve in ROI scan.

DESCRIPTION OF EMBODIMENTS

Figure 2:
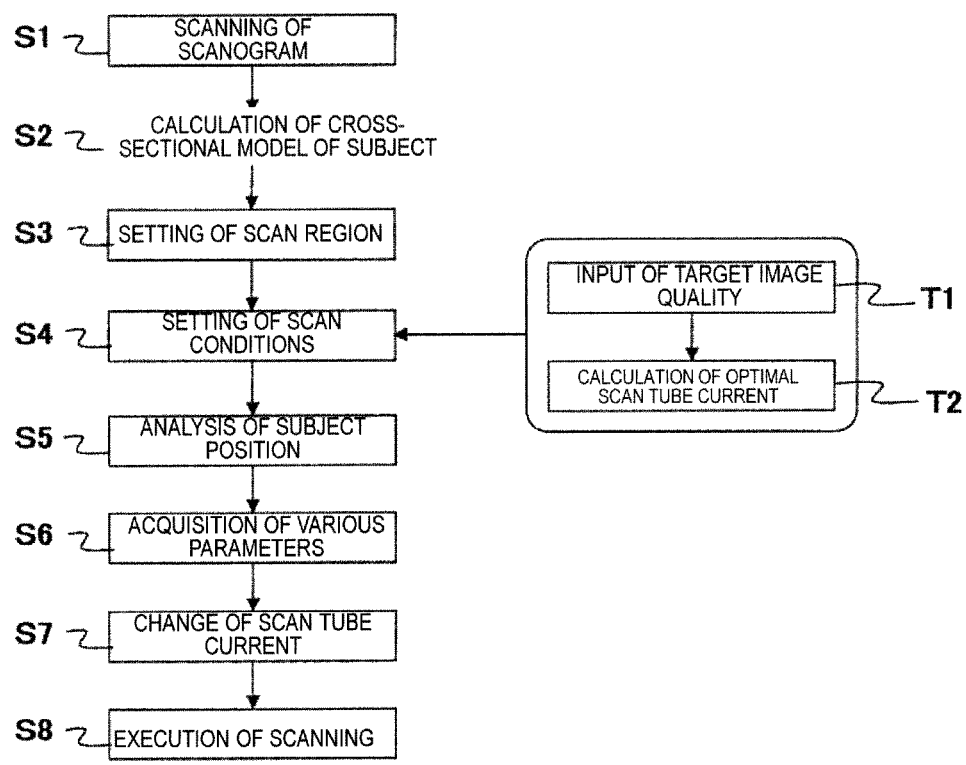
FIG. 2 is an operation flow chart in a best mode for executing the present invention.

Hereinafter, preferred embodiments of the present invention will be described according to the accompanying drawings. In addition, the present invention is not limited to the embodiments shown below.

An X-ray CT apparatus to which the present invention is applied will be described using the drawings.

FIG. 1 is a view showing the entire configuration of an X-ray CT apparatus 1 to which the present invention is applied. The X-ray CT apparatus 1 includes a scan gantry 100 and a console 120.

The scan gantry 100 includes: an X-ray tube 101 which is an X-ray source that emits X-rays while rotating around a subject; a rotary disk 102; a collimator 103; a compensation filter 126 which adjusts at least one of the output distribution and the spectral distribution of the X-rays emitted from the X-ray source to the subject; an X-ray detector 106 which is disposed opposite to the X-ray source with the subject interposed therebetween, rotates together with the X-ray source, and detects the amount of X-rays transmitted through the compensation filter and the subject; a data collector 107; a bed 105; a gantry controller 108; a bed controller 109; and an X-ray controller 110. The X-ray tube 101 is a device which emits X-rays to the subject placed on the bed 105. The collimator 103 is a device which restricts the irradiation range of X-rays emitted from the X-ray tube 101. The X-ray detector 106 is a device which is disposed opposite to the X-ray tube 101 and detects X-rays transmitted through the subject. The rotary disk 102 includes an opening 104 through which the subject placed on the bed 105 is inserted and also includes the X-ray tube 101 and the X-ray detector 106 mounted therein, and rotates around the subject. The data collector 107 is a device which collects the amount of X-rays detected by the X-ray detector 106 as digital data. The gantry controller 108 is a device which controls the rotation of the rotary disk 102. The bed controller 109 is a device which controls up and down and front and rear movements of the bed 105. The X-ray controller 110 is a device which controls an output to the X-ray tube 101.

The console 120 includes: an input device 121; an image operation device 122 serving as an image reconstructing unit or the like which reconstructs a tomographic image of the subject on the basis of the detected amount of X-rays; a display device 125 which displays a tomographic image or a scanogram image; a storage device 123; and a system controller 124. The input device 121 is a device for inputting the name of the subject, examination date and time, scanning conditions, and the like. Specifically, the input device 121 is a keyboard or a pointing device. The image operation device 122 is a device which reconstructs a CT image by performing arithmetic processing on the measurement data transmitted from the data collector 107. The display device 125 is a device which displays the CT image or the scanogram image created by the image operation device 122. Specifically, the display device 125 is a CRT (Cathode-Ray Tube), a liquid crystal display, or the like. The storage device 123 is a device which stores the data collected by the data collector 107 and the image data of the CT image created by the image operation device 122. Specifically, the storage device 123 is an HD (Hard Disk) or the like. The system controller 124 (control unit) controls these components, that is, the gantry controller 108, the bed controller 109, the X-ray controller 110 or the X-ray source, the compensation filter 126, the X-ray detector 106, the image operation device 122, and the like and controls the measurement of a tomographic image of the subject and scanogram projection data.

The X-ray tube 101 is controlled by the X-ray controller 110, and emits X-rays based on the scanning conditions (X-ray tube voltage, X-ray tube current, and the like) input through the input device 121. The X-ray detector 106 is formed by arraying a plurality of (for example, about 1000) X-ray detecting elements in the circumferential direction of the rotary disk 102 or arraying them in a two-dimensional direction of the circumferential direction of the rotary disk 102 and the rotary axis direction of the rotary disk 102, and detects X-rays, which are emitted from the X-ray tube 101 and transmitted through the subject, by the plurality of elements. The rotary disk 102 is controlled by the gantry controller 108 and rotates on the basis of the scanning conditions (rotation speed and the like) input through the input device 121. The bed 105 is controlled by the bed controller 109 and operates on the basis of the scanning conditions (helical pitch and the like) input through the input device 121.

X-ray emission from the X-ray tube 101 and detection of transmitted X-rays by the X-ray detector 106 are repeated while the rotary disk 102 is rotating. As a result, the projection data from various angles is acquired. The acquired projection data from various angles is transmitted to the image operation device 122. The image operation device 122 reconstructs a CT image by performing back projection processing on the transmitted projection data from various angles. The CT image obtained by reconstruction is displayed on the display device 125.

The standard procedure for acquiring a tomographic image required for diagnosis will be described using the X-ray CT apparatus 1.

(1) A projected image called a scanogram image is scanned prior to the main scanning. In order to scan a scanogram image, X-rays are emitted from the X-ray tube 101 to the subject while moving the bed 105 in the rotary axis direction of the rotary disk 102 in a state where the rotary disk 102 is stopped. The X-rays transmitted through the subject are detected as the amount of transmitted X-rays by the X-ray detector 106. A scanogram image is acquired on the basis of the amount of transmitted X-rays which is detected every position of the bed.

(2) The acquired scanogram image is displayed on the display device 125. The operator sets the scanning position and the scanning range at the time of main scanning on the scanogram image using the input device 121.

(3) Main scanning is performed on the basis of the scanning position and the scanning range set on the scanogram image.

First Embodiment

FIG. 2 shows a flow chart of a series of operations in scanning (scanning) related to a first embodiment of the present invention. Hereinafter, each step in FIG. 2 will be described in the order of the steps.

(Step S1)

The X-ray CT apparatus 1 acquires the scanogram projection data by performing scanogram scanning of the subject under control of the system controller 124 and creates a scanogram image. X-rays are emitted to the subject in one direction (for example, from the back to the front) without rotating the X-ray tube, and the scanogram projection data is acquired by the detector. The X-ray CT apparatus 1 creates a scanogram image by transmitting the scanogram projection data to the image operation device 122 and displays it on the display device 125. This scanogram image is created when an image of X-rays transmitted from the back to the front is viewed from one direction, for example.

(Step S2)

Then, the scanogram projection data is analyzed by a cross-sectional model calculating unit which is built in the image operation device 122 and which calculates a cross-sectional model of the subject on the basis of the scanogram projection data. As a result, a cross-sectional model of the subject is calculated. The cross-sectional model of the subject is formed by approximating the cross section of the subject, which corresponds to each slice position, as an elliptical cross section having an X-ray absorption coefficient equivalent to that of water, for example.

(Step S3)

On the basis of the scanogram image, the operator sets a scan region using the input device. The scan region indicates a slice position of the subject at the time of scanning, a scan start position, and a scan end position.

(Step S4)

The operator sets the scan conditions after setting the scan region. The scan conditions include the type of compensation filter used according to the physique of the subject to be examined, the moving pitch of the bed, scan time, the X-ray collimation conditions, the type of reconstruction filter function, and the field-of-view size, for example. The set scan region and the set scan conditions are stored in the storage device 123.

In addition, when the operator performs scanning using the CT-AEC, the target image quality is input in step T1. The target image quality is a standard deviation of the CT value in a CT image (hereinafter, image SD (standard deviation)), for example. Then, in step T2, an optimal scan tube current mA_opt (N) is calculated every slice position N in the scan range of the subject in order to realize the target image quality input by the operator (here, refer to PTL 3 for a method of calculating the optimal scan tube current, for example).

Figure 3:
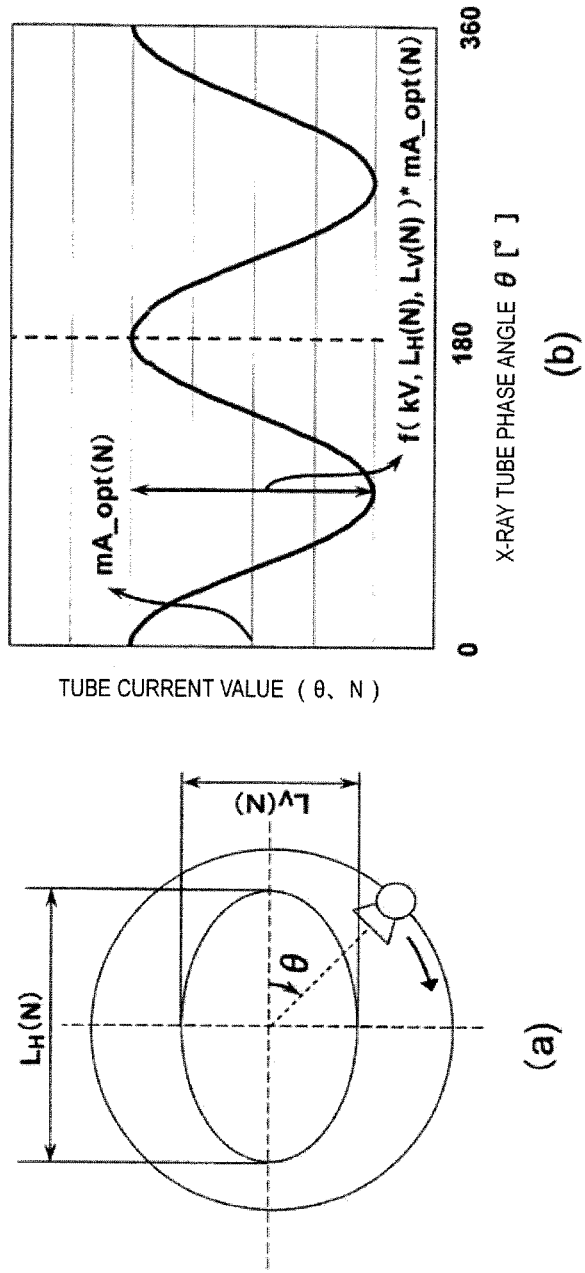
FIG. 3 is a schematic view showing a cross-sectional model of the subject and a scan tube current.

Here, the calculation expression and the schematic shape of the scan tube current at the slice position N become Expression 1 and FIG. 3, respectively, for example, by an X-ray tube current modulation pattern calculating unit which is built in the image operation device 122 and which calculates an X-ray tube current modulation pattern indicating a time-series change of X-ray irradiation on the basis of the cross-sectional model of the subject. FIG. 3(a) is a schematic view of the horizontal and vertical lengths of an elliptical cross-sectional model and the X-ray tube rotation phase, and FIG. 3(b) is the relationship between the X-ray tube phase angle and a scan tube current.

$$mA(\theta, N) = mA\_opt(N) + \frac{f(kV, L_H(N), L_V(N))}{2} * mA\_opt(N) * \cos\left(\frac{\pi * \theta}{90}\right)$$ [Expression 1]

$mA(\theta, N)$: scan tube current when the X-ray tube phase angle is $\theta$ and the slice position is N $f(kV, L_H(N), L_V(N))$: amplitude of the scan tube current, and can be expressed as a function of the following parameters kV: scan tube voltage $L_H(N)$: horizontal length of the cross-sectional model of the subject at the slice position N $L_V(N)$: Vertical length of the cross-sectional model of the subject at the slice position N $mA(\theta, N)$ expresses a change in the tube current with a shape of a cosine wave which has an average tube current value of mA_opt(N).

(Step S5)

Then, the subject position at each slice position is analyzed. More specifically, the amount of displacement between the rotation center of the X-ray source and the desired position of the cross-sectional model is calculated by a displacement amount calculating unit which is built in the image operation device 122 and which calculates the amount of displacement between the rotation center of the X-ray source and the desired position of the cross-sectional model. The displacement amount calculating unit calculates the amount of displacement including at least either a vertical component or a horizontal component every slice position. For the calculation of the subject position, the cross-sectional model of the subject calculated in step S2 is used. The central position of the cross-sectional model is calculated, and the amount of displacement δ between the subject center and the rotation center of the X-ray tube is analyzed in the horizontal and vertical directions every slice position. Here, it is assumed that the amount of displacement between the subject center and the rotation center of the X-ray tube in the horizontal direction is $\delta_{LH}$ and the amount of displacement between the subject center and the rotation center of the X-ray tube in the vertical direction is $\delta_{LV(N)}$.

Specifically, a method is preferable in which the rotation center of the X-ray tube and the horizontal and vertical positions of the bed are stored as internal parameters of the system controller 124 and the amount of displacement described above is calculated from the geometrical relationship with the center of the cross-sectional model.

Figure 4:
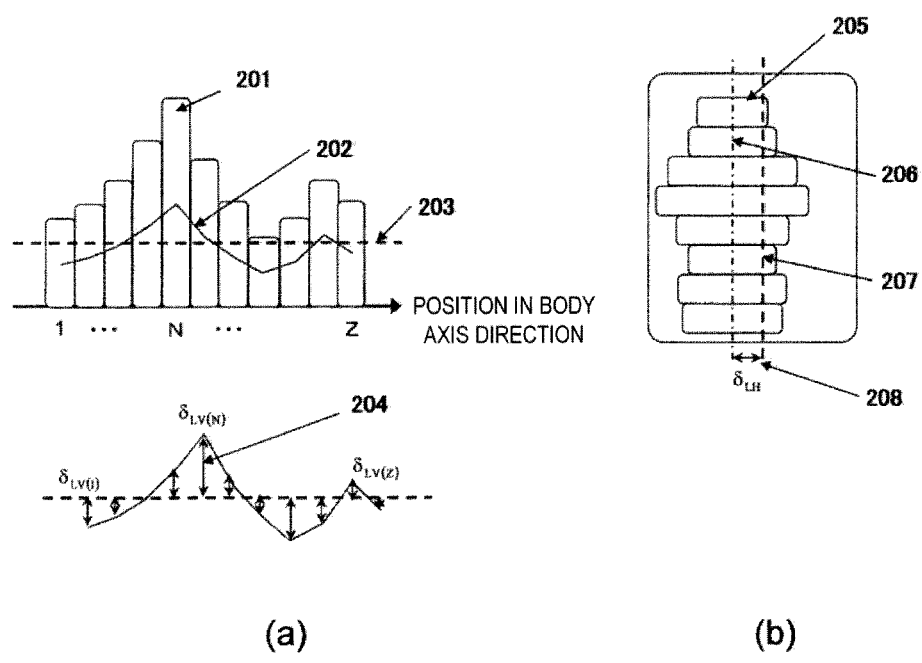
FIG. 4 is a conceptual view showing the amount of displacement between the center of the cross-sectional model of the subject and the center of X-ray tube rotation.

At the upper side in FIG. 4(*a*), a schematic view showing the amount of displacement between the center of the cross-sectional model of the subject in the vertical direction and the center of X-ray tube rotation is shown. 201 is a cross-sectional model in the vertical direction estimated on each slice position. As shown by a polygonal line indicated by 202, it is shown that the position of the center of the cross-sectional model in a direction vertical to the bed changes with each slice position.

Here, 203 is the center of X-ray tube rotation at the initial bed height Y0.

In the drawing shown at the lower side in FIG. 4(*a*), 204 indicates the calculation of the amount of displacement $\delta_{LV}$(N) of each slice position. An example is shown in which the center of the cross-sectional model swings up and down from the center of X-ray tube rotation by each slice.

FIG. 4(*b*) is a schematic view showing the center (206) of a cross-sectional model of the subject (205) in the horizontal direction and the amount of displacement (208) from the center of X-ray tube rotation (207). According to FIG. 4(*b*), it can be seen that the subject deviates by $\delta_{LH}$(208) in the horizontal direction. In addition, it is preferable that the amount of displacement have a positive or negative sign with respect to the center of X-ray tube rotation. For example, the positive amount of displacement in the vertical direction can be defined as a case where the center of the cross-sectional model of the subject is located above the center of X-ray tube rotation.

(Step S6)

In step S6, various parameters are acquired. The acquired parameters include at least Y0, $L_H$(N), $L_V$(N), $\delta_{LH}$, and $\delta_{LV(N)}$, and also include information regarding the compensation filter shape. Here, Y0 is an initial height position of the bed.

(Step S7)

Using the various parameters acquired in step S6, the scan tube current calculated in step T1 is changed. The inventors have found out the following from the unique experiment.

FIG. 5(*b*) shows how the relative image SD of a central portion of a cross-sectional model of the subject changes with the positional displacement (δ) of the center of X-ray tube rotation, when a predetermined cross-sectional model is used, for each compensation filter (WS, MS, NS) used in each case where the size of the subject shown in FIG. 5(*a*) is large (WS), medium (MS), and small (NS). According to FIG. 5(*b*), it can be seen that the image SD increases according to an increase in the absolute value of the amount of displacement and the image quality deteriorates accordingly in all cases where the compensation filter is WS, MS, and NS. However, it can be seen that the change rate of the relative image SD according to an increase in the amount of displacement is small in the case of a large subject for whom the shape of the compensation filter does not change steeply.

In addition, FIG. 6(*b*) shows how the relative image SD changes with the change of the amount of displacement when the size of the subject is large (LP), medium (MP), and small (SP). In all cases where the size of the subject is large (LP), medium (MP), and small (SP), the relative image SD increases according to an increase in the amount of displacement. In addition, it can be seen that the larger the subject, the smaller the change rate of the relative image SD.

Here, a horizontal component and a vertical component may be considered as the amount of displacement δ. However, the horizontal axes shown in FIGS. 5(*b*) and 6(*b*) may be expressed as δ by calculating $\sqrt{(\delta_{LH}^2 + \delta_{LV(N)}^2)}$ from both the horizontal and vertical components, for example.

In this step, a change rate of the relative image SD to the amount of displacement δ when a certain compensation filter is used for a subject of a certain size is experimentally acquired as a table or a function in advance and is stored in the storage means 123, and mA_opt(N) is corrected as in Expression 2 on the basis of the table or the function.

$$mA\_mod\ u(N) = (SD(filter, size, \delta))^2 * mA\_opt(N) \quad [\text{Expression 2}]$$

Expression 2 is for reducing an increase in the relative image SD according to the amount of displacement by increasing the tube current. Here, the increase in the relative image SD is a function of the kind of compensation filter (filter), the size of the subject (size), and the amount of displacement (δ), and mA_mod u(N) of each slice position is calculated by multiplying the square of the function by mA_opt(N).

Since Expression 2 is written as a case where the average tube current value at each slice position changes discretely herein, Expression 2 is applied to all slice positions in a scan region and used to calculate an optimal scan tube current.

However, in the case of a scanning method in which X-rays are continuously emitted to the subject as in the helical scan, it is preferable to change the tube current modulation curve (Expression 1) so that the tube current changes continuously between slices.

Moreover, for the data in FIG. 5, a method is practically desirable in which the relative image SD, when a compensation filter has been changed under the condition of the amounts of displacement of several points, is acquired in advance and the tube current is changed using the relative image SD after function approximation or interpolation. Similarly, also for the data in FIG. 6, experiments are performed in advance under the condition of the amounts of displacement of several points using several kinds of phantoms which diagnose the subject size as an ellipse equivalent to water, and the relative image SD is acquired. Then, a method is practically desirable in which the relative image SD is calculated by performing function approximation or interpolation of the acquired data and the tube current is changed using the calculated relative image SD. The optimal scan tube current after change at the slice position N is obtained by replacing mA_opt (N) with mA_mod u(N) in Expression 1.

(Step S8)

In step S8, scanning is executed using the changed scan tube current calculated in step S7.

Through such processing, even if the cross-sectional model of the subject and the center of X-ray tube rotation deviate from each other in the vertical direction or in the horizontal direction, a desired image SD when a central portion of an image (central portion of the subject) is an object to be diagnosed is realized by appropriately changing the scan tube current value calculated in advance, for example. That is, the X-ray CT apparatus related to the present embodiment includes a compensation unit which compensates for deterioration of the image quality, which is based on the amount of displacement between the rotation center of the X-ray source and the desired position of the cross-sectional model, by changing an X-ray tube current modulation pattern.

Here, the desired position is a central position of the cross-sectional model, and the position for compensation for deterioration of the image quality is a central portion of a tomographic image of the subject. Moreover, in the present embodiment, the change of the X-ray tube current modulation pattern is performed every slice position, and deterioration of the image quality is expressed by an increase in the standard deviation of a central portion of a tomographic image. In addition, the relationship between the amount of displacement and the deterioration of image quality expressed by an increase in the standard deviation is experimentally acquired in advance and stored in a storage device, and the X-ray tube current modulation pattern is changed using the increase rate of a standard deviation based on the amount of displacement calculated from the relationship. In addition, the amount of displacement includes a component in the vertical direction and a component in the horizontal direction.

Therefore, it is possible to perform scanning without reducing the diagnostic ability. Moreover, in the present embodiment, a subject moving unit which will be described later in the following embodiment is not necessary. In the present embodiment, it is possible to prevent an accident in which the optimal bed position is beyond the bed operation range of the X-ray CT apparatus or an accident in which the subject comes in contact with the X-ray CT apparatus during the scan due to moving the bed before starting the scan.

Second Embodiment

Figure 7:
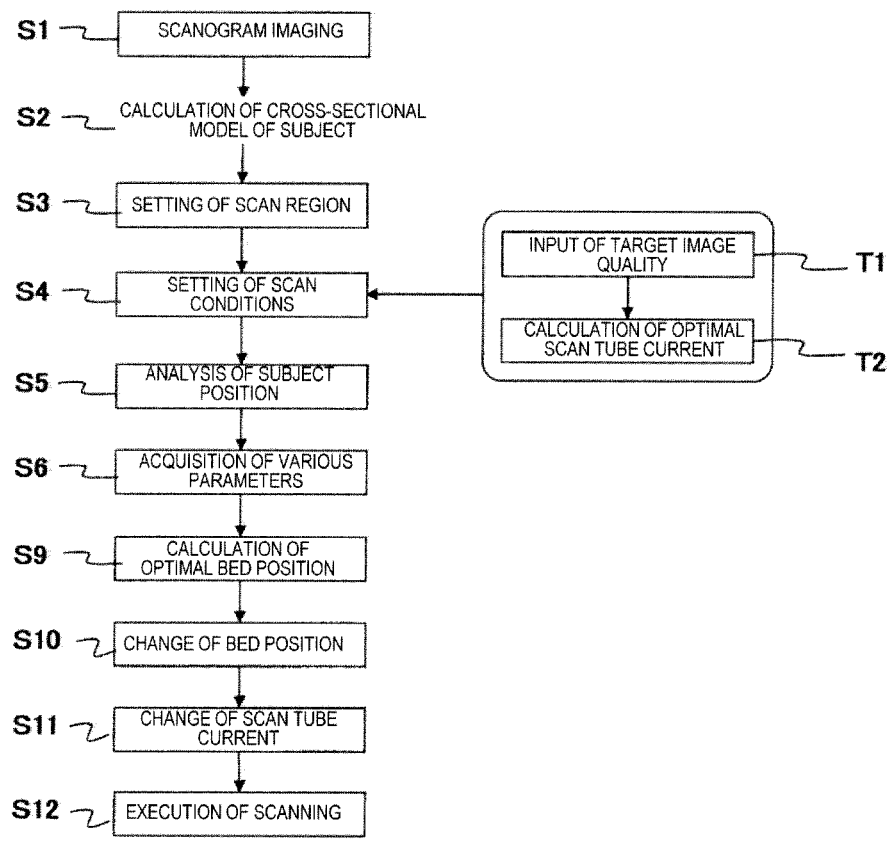
FIG. 7 is an operation flow chart in a second embodiment.
Figure 8:
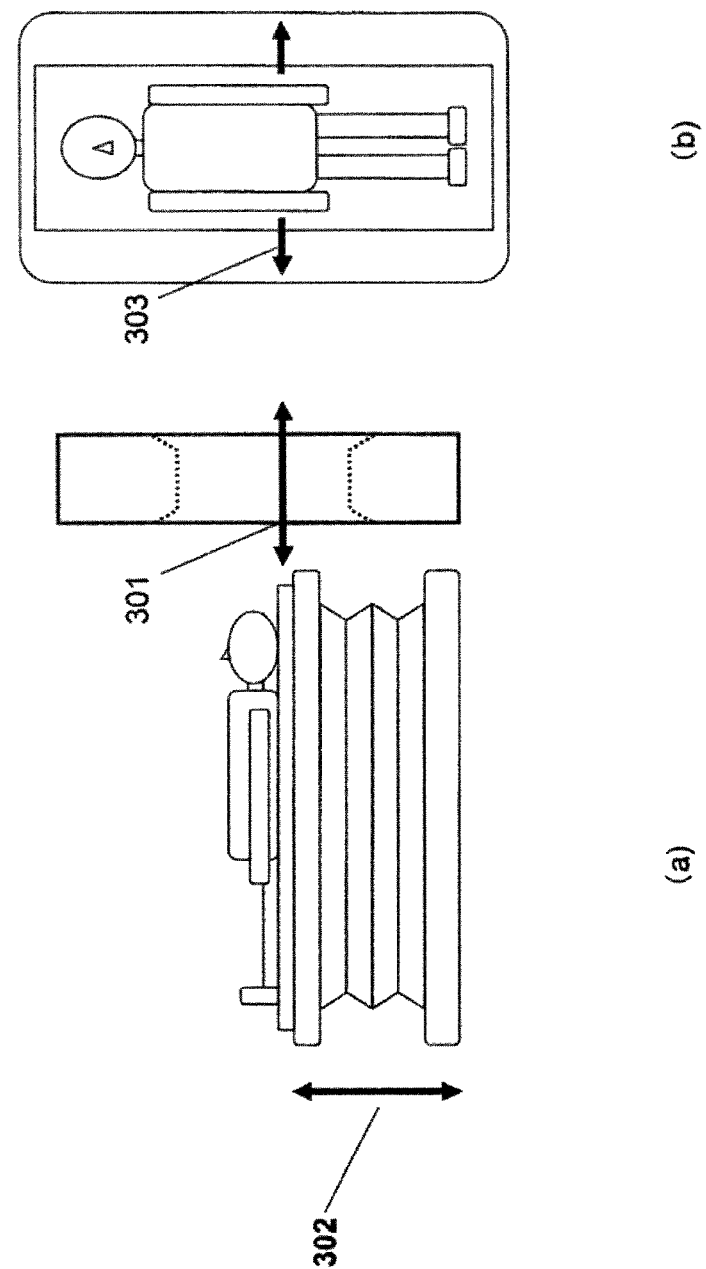
FIG. 8 is a schematic view of bed driving of an X-ray CT apparatus used in the present invention.

Next, a second embodiment will be described using the operation flow chart in FIG. 7. The operation flow in the second embodiment is basically the same as that in the first embodiment. However, in the case of a bed of an X-ray CT apparatus used in the present embodiment, not only horizontal movement (301) in the body axis direction of the subject and vertical movement (302) as in the related art are possible as shown in FIG. 8(a), but also left and right movement (303) in the body width direction of the subject is possible as shown in FIG. 8(b).

(Step S1) to (Step S6)

Steps S1 to S6 are the same processing as in the first embodiment. However, in step S6, it is necessary to newly acquire a parameter X0. X0 is an initial position of the bed in the left and right direction.

(Step S9)

In step S9, the optimal bed position is calculated on the basis of the parameter acquired in step S6. First, the optimal bed height is expressed as (Y0-$\epsilon_V$). Here, $\epsilon_V$ is given by Expression 3, and means a result obtained by dividing the sum of the amount of displacement of each slice position by the number of slices, that is, an average value of the amounts of displacement in all slices.

$$\varepsilon_V = \frac{\sum_{N=1}^{Z} \delta_{LV(N)}}{Z}$$ [Expression 3]

Next, the amount of movement $\epsilon_H$ to the optimal bed position in the body width direction (left and right direction) of the subject is given as the same position as the center of X-ray tube rotation. That is, $\epsilon_H=\delta_{LH}$ is assumed.

(Step S10)

Figure 9:
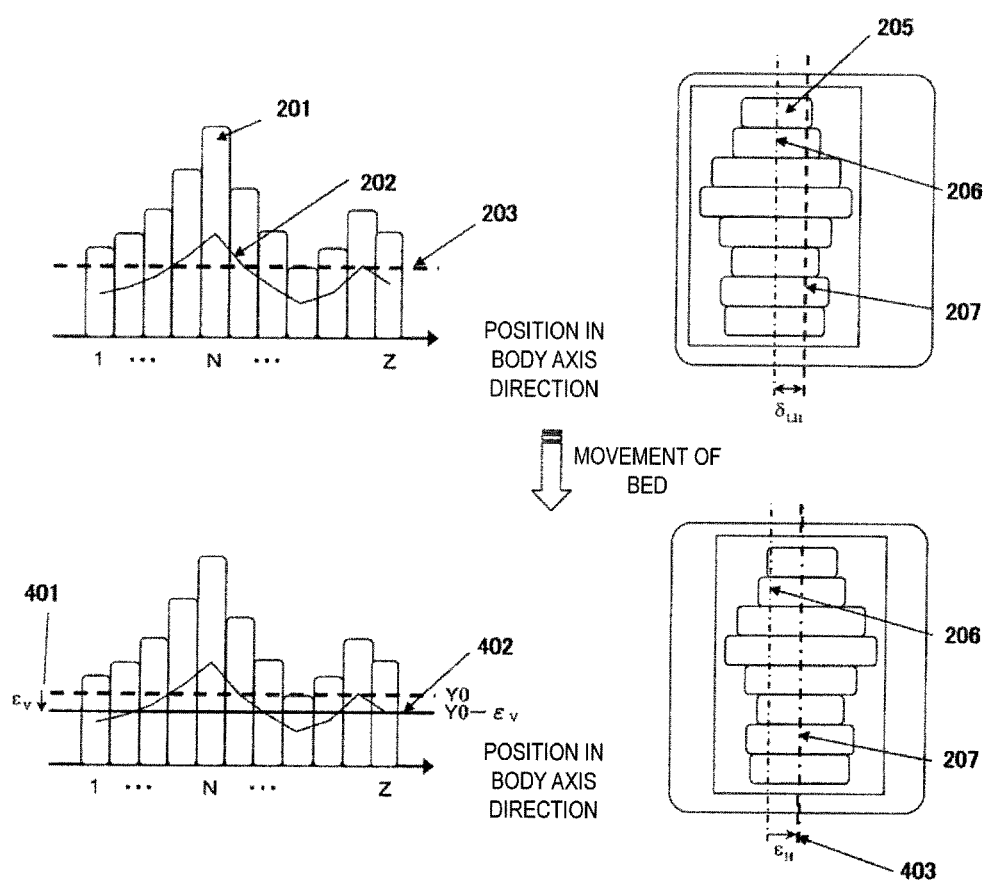
FIG. 9 is a conceptual view regarding moving the bed position on the basis of the amount of displacement between the center of a cross-sectional model of the subject and the center of X-ray tube rotation.

Using the optimal bed position calculated in step S9, the bed position is changed as shown in FIG. 9. More specifically, in the vertical direction, the position of the bed is changed by a subject moving unit which moves the subject in the opposite direction to the amount of displacement ($\epsilon_V$) in the vertical direction (401). 402 is a rotation center at the changed bed height. Moreover, in the left and right direction, the position of the bed is changed by a subject moving unit which moves the subject in the opposite direction to displacement by the amount of displacement ($\delta_{LH}$) in the left and right direction (403). Change of the bed position can be easily realized by using mechanisms for movements of the bed in the vertical and left and right directions.

(Step S11)

In this step, the same processing as in step S7 in the first embodiment is performed. However, for the amount of displacement $\delta$ at the slice position N, it is preferable to consider only the amount of displacement between the center of the cross-sectional model of the subject and the center of X-ray tube rotation in the bed height direction since the bed position is changed in step S10. The amount of displacement $\delta'_{LV(N)}$ of each slice position is given by the following Expression 4.

$$\delta'_{LV(N)}=\delta_{LV(N)}-\epsilon_V$$ [Expression 4]

The tube current is changed by applying this amount of displacement to the table or the function prepared as in FIGS. 5 and 6. Specifically, this is calculated in the same manner as in Expression 2.

(Step S12)

Scanning is executed on the basis of the scan tube current calculated in step S11.

Through such processing, even if the average height of the rotation center of the cross-sectional model of the subject and the center of X-ray tube rotation deviate from each other in the vertical direction or in the left and right direction, processing of suppressing the amount of displacement at each slice position to the minimum by changing the bed position (moving the position of the subject) is added. Then, by appropriately changing the scan tube current value calculated in advance, a desired image SD is realized when a central portion of an image is a reference for diagnosis, for example. Therefore, it becomes possible to perform scanning without reducing the diagnostic ability. In addition, in the present embodiment, the scan tube current is changed in step S9. On the other hand, since the average amount of displacement is a minimum in all slices even if the scan tube current is not changed, degradation of the image quality in the sequence is suppressed to the minimum. Accordingly, a method of performing scanning only by changing the bed position may be used. In addition, the first embodiment and the present embodiment may be used in combination. For example, in the case of correcting the scan tube current without changing the bed position according to the amount of displacement, it is preferable to correct the scan tube current after changing the bed position when the amount of tube current which can be output is exceeded or the like.

Third Embodiment

Figure 10:
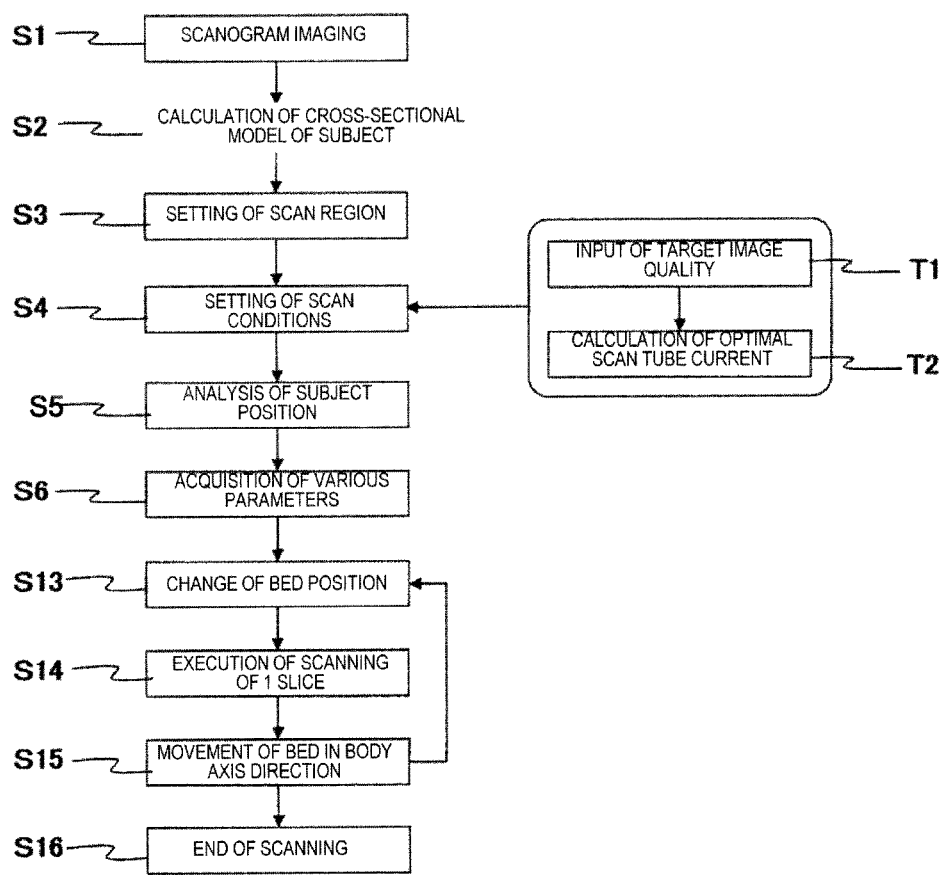
FIG. 10 is an operation flow chart in a third embodiment.

Next, a third embodiment will be described using the operation flow chart in FIG. 10. The operation flow in the third embodiment is for explaining an operation only in normal scan in which a bed (subject moving unit) is moved every slice for scanning. Basically, the third embodiment is the same as the first and second embodiments, but the operation after acquisition of various parameters is different.

(Step S1) to (Step S6)

Steps S1 to S6 are the same processing as in the second embodiment.

(Step S13)

In step S13, the bed position is changed so that the amount of displacement acquired in step S6 becomes 0 at the first slice position in the corresponding sequence.

(Step S14)

In step S14, scanning of 1 slice is executed at the bed position changed in step S13.

(Step S15)

In step S15, the bed is moved to the next slice position in the body axis direction. Then, the process proceeds to step S13, and the process of steps S14 and S15 is performed by the number of slices in the corresponding sequence.

(Step S16)

scanning in all slice positions is ended.

Through such processing, even if the cross-sectional model of the subject and the center of X-ray tube rotation are displaced from each other in the vertical direction or in the left and right direction, processing of setting the amount of displacement to 0 by changing the bed position every slice position is added. Then, by performing scanning with the scan tube current value calculated in advance, a desired image SD is realized when a central portion of an image is a reference for diagnosis, for example. That is, the X-ray CT apparatus related to the present invention includes the subject moving unit which moves the subject every slice position so that the central position of the cross-sectional model of the subject becomes the rotation center of the X-ray source, and this serves as a compensation unit which compensates for deterioration of the image quality based on the amount of displacement between the rotation center of the X-ray source and the desired position of the cross-sectional model. Therefore, it becomes possible to perform scanning without reducing the diagnostic ability.

Fourth Embodiment

Figure 11:
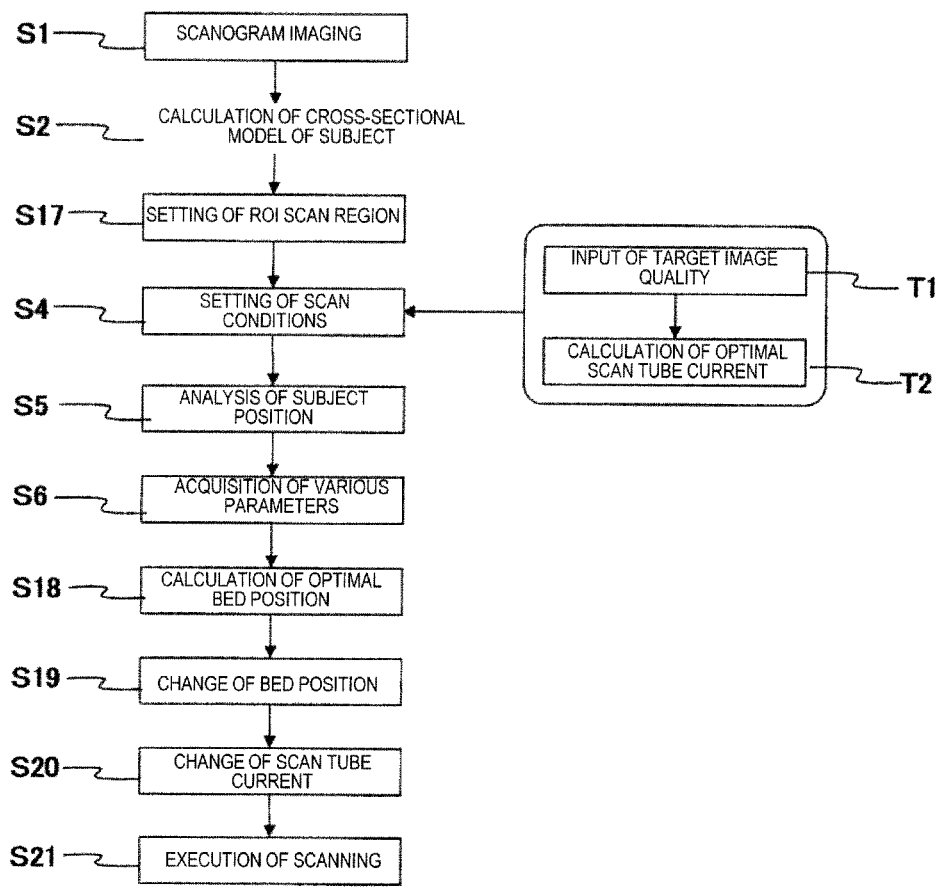
FIG. 11 is an operation flow chart in a fourth embodiment.

Next, a fourth embodiment will be described using the operation flow chart in FIG. 11. The operation flow in the fourth embodiment is basically the same as that in the second embodiment.

(Step S1) and (Step S2)

Steps S1 and S2 are the same processing as in the second embodiment.

(Step S17)

In step S17, scan region setting in the case of performing scanning only in a local region is performed. For example, in the case of scanning the heart, scan region setting for setting an ROI (Region of interest) 501 on a scanogram as in FIG. 12 may be considered.

(Step S4) to (Step S6)

Steps S4 to S6 are the same processing as in the second embodiment.

(Step S18) and (Step S19)

Figure 13:
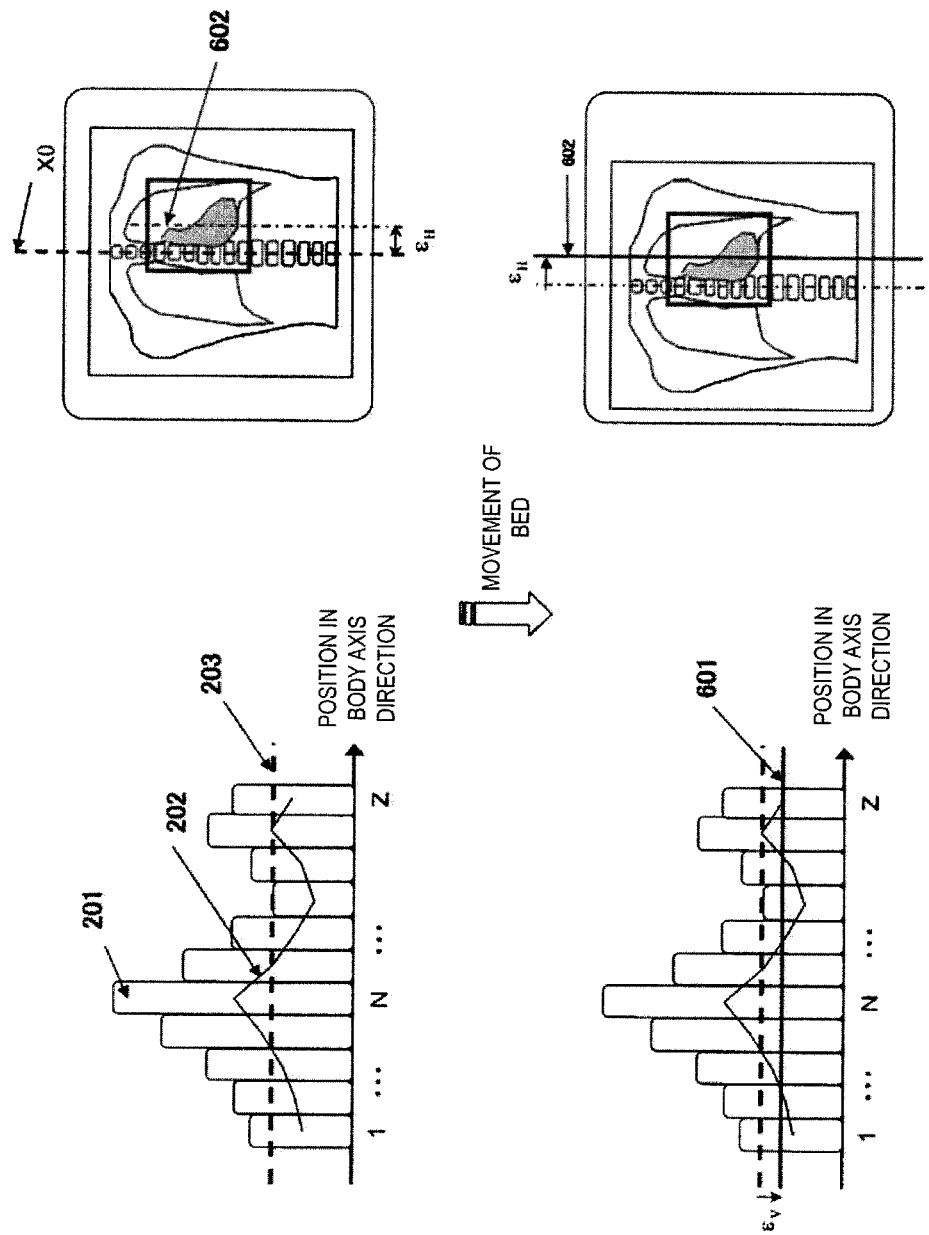
FIG. 13 is a conceptual view regarding calculation of the optimal bed position in the case of ROI scan.

In steps S18 and S19, calculation and movement of the optimal bed position are performed on the basis of various parameter information acquired in step S6. Specifically, these are performed as in FIG. 13.

First, the optimal bed position in the bed height direction is calculated as in the second embodiment. That is, the optimal bed position in the bed height direction is given as $(Y0-\epsilon_V)$. 601 is a rotation center at the changed bed height.

Then, the optimal position of the bed in the left and right direction is set such that the center of X-ray tube rotation and the central axis (602) of a scan region in ROI scan are the same. That is, the optimal bed position in the left and right direction is given by $(+\epsilon_H)$.

X0: initial position of a bed in the left and right direction

Figure 14:
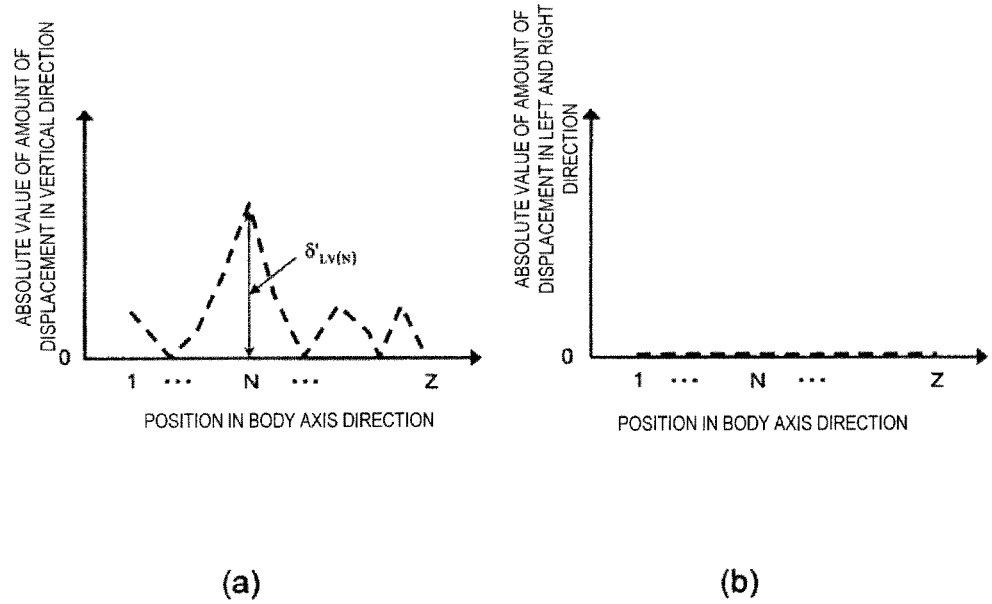
FIG. 14 is a graph regarding the amount of displacement between the center of X-ray tube rotation at the optimal bed position and the center of a cross-sectional model of the subject in ROI scan.

Y0: initial position of a bed in the vertical direction $\epsilon_H$: amount of displacement between the center of X-ray tube rotation in the left and right direction and the central axis of the ROI scan region $\epsilon_V$: average value of the amount of displacement of the center of the cross-sectional model of the subject in the bed height direction in all slices FIG. 14 shows an absolute value of the amount of displacement between the center of X-ray tube rotation and the center of a cross-sectional model of the subject at the optimal bed position. The amount of displacement $\delta'_{LV(N)}$ in the vertical direction is given in the same manner as in Expression 4 in FIG. 14(a). On the other hand, for the absolute value of the amount of displacement in the left and right direction, the amount of displacement may be considered to be 0 since the rotation center in ROI scan is a target of the image quality of a cross-sectional model of the subject as shown in FIG. 14(b).

(Step S20)

Using the amount of displacement calculated in step S18, the scan tube current is changed. FIG. 15(b) schematically shows a scan tube current modulation curve at the time of ROI scan. When the center of the cross-sectional model of the subject and the center of X-ray tube rotation are the same, the scan tube current is expressed by Expression 1. On the other hand, when the bed has been moved by $\epsilon_H$ in the left and right direction in order to perform the ROI scan, the path length of X-rays transmitted through the cross-sectional model of the subject changes as in the schematic view of horizontal and vertical lengths of the elliptical cross-sectional model and the X-ray tube rotation phase shown in FIG. 15(a). Accordingly, the scan tube current should be changed as in Expression 5.

$$mA'(\theta, N) = mA\_opt'(N) + \frac{f(kV, L_H(N), L_V'(N))}{2} * mA\_opt'(N) * \cos\left(\frac{\pi * \theta}{90}\right) \quad [\text{Expression 5}]$$

Here, mA'(θ, N): scan tube current when the X-ray tube phase angle is θ and the slice position is N at the time of ROI scan f(kV, $L_H$(N), $L_V$'(N)): amplitude of a scan tube current at the time of ROI scan, and can be expressed as a function of the following parameters kV: scan tube voltage $L_H$(N): horizontal length of the cross-sectional model of the subject at the slice position N $L_V$'(N): Vertical length of the cross-sectional model of the subject at the slice position N when movement by $\epsilon_H$ in the left and right direction has been made mA'(θ, N) expresses a change in the tube current with a shape of a cosine wave which has an average tube current value of mA_opt'(N). In addition, mA_opt'(N) is changed in order to correct the influence of an increase in the relative image SD according to the amount of displacement between the center of X-ray tube rotation in the bed height direction and the center of the cross-sectional model of the subject. Assuming that the value after change is mA_mod u'(N), it is expressed by Expression 6.

$$mA\_mod\ u'(N) = (SD(\text{filter}, \text{size}, \delta))^2 * mA\_opt'(N) \quad [\text{Expression 6}]$$

Expression 6 is for reducing the increase in the relative image SD according to the amount of displacement in the bed height direction by increasing the tube current. Here, the increase in the relative image SD is a function of the kind of a compensation filter (filter), the size of the subject (size), and the amount of displacement (δ).

(Step S21)

Scanning is executed using the calculated scan tube current after change.

Through such processing, even if the cross-sectional model of the subject and the center of X-ray tube rotation are displaced from each other in the up and down and left and right directions in the case of ROI scan, processing of suppressing the amount of displacement to the minimum by changing the bed position is added. Then, by appropriately changing the scan tube current value calculated in advance, a desired image SD is realized when a central portion of an image is a reference for diagnosis, for example. That is, the X-ray CT apparatus related to the present invention includes the ROI setting unit which sets an ROI on a scanogram image and the subject moving unit which moves the subject such that the center of the ROI becomes the rotation center of the X-ray source.

Therefore, it becomes possible to perform scanning without reducing the diagnostic ability. In addition, in the present embodiment, the scan tube current is changed in step S20. On the other hand, since the average amount of displacement is a minimum in the corresponding sequence even if the change of a scan tube current shown in Expression 6 is not performed, degradation of the image quality in the sequence is suppressed to the minimum. Accordingly, a method of performing scanning only by the change of the scan tube current shown in Expression 5 may be used. Then, by performing scanning with the calculated scan tube current value, a desired image SD is realized when a central portion of an image is a reference for diagnosis, for example. Therefore, it is possible to perform scanning without reducing the diagnostic ability.

While the present invention has been described on the basis of the four embodiments, the technical range of the present invention is not limited to the embodiments described above. It is apparent to those skilled in the art that various changes or modifications can be made within the range of the technical idea disclosed in this application, and it should be understood that they also without doubt belong to the technical range of the present invention.

INDUSTRIAL APPLICABILITY

The present invention can be used for an X-ray CT apparatus capable of acquiring a more high-quality CT image by appropriately setting the bed position or a change pattern of the tube current during scanning according to the positional displacement between the subject and a compensation filter.

REFERENCE SIGNS LIST

S1: scanogram imaging
S2: calculation of cross-sectional model of the subject
S3: setting of scan region
S4: setting of scan conditions
S5: analysis of subject position
S6: acquisition of various parameters
S7: change of scan tube current
S8: execution of scanning

The invention claimed is:

1. An X-ray CT apparatus comprising:
   an X-ray source which emits X-rays while rotating around a subject;
   a compensation filter which adjusts at least one of output distribution and spectral distribution of the X-rays emitted from the X-ray source to the subject;
   an X-ray detector which is disposed opposite to the X-ray source with the subject interposed therebetween, rotates together with the X-ray source, and detects an amount of X-rays transmitted through the compensation filter and the subject;
   an image operation unit which reconstructs a tomographic image of the subject on a basis of the detected amount of X-rays;
   a display unit which displays the tomographic image;
   a control unit which controls each of the constituent components;
   a compensation unit which compensates for deterioration of image quality, which is based on an amount of displacement between a rotation center of the X-ray source and a desired position of the subject, by changing an X-ray tube current modulation pattern indicating a time-series change of emission of the X-rays and/or by moving the position of the subject; and
   a storage unit which stores a relationship between the amount of displacement and the deterioration of the image quality, the relationship having been experimentally acquired in advance,
   wherein the compensation unit compensates for the deterioration of image quality, by referring to the relationships stored in the storage unit.

2. The X-ray CT apparatus according to claim 1, characterized by further comprising:
   a cross-sectional model calculating unit which calculates a cross-sectional model of the subject on the basis of scanogram projection data obtained by control of the control unit,
   wherein the desired position is a central position of the cross-sectional model, and a position for compensating the deterioration of the image quality is the center of the tomographic image of the subject.

3. The X-ray CT apparatus according to claim 2, characterized by further comprising:
   an X-ray tube current calculating unit which calculates an X-ray tube current modulation pattern on the basis of the cross-sectional model.

4. The X-ray CT apparatus according to claim 1,
   characterized in that the change of the X-ray tube current modulation pattern is performed every slice position.

5. The X-ray CT apparatus according to claim 2,
   characterized in that the deterioration of the image quality is expressed as an increase in a standard deviation of the center of the tomographic image.

6. The X-ray CT apparatus according to claim 1,
   wherein the relationship between the amount of displacement and the deterioration of the image quality is a function of a type of the compensation filter and a size of the subject.

7. The X-ray CT apparatus according to claim 5,
   wherein the X-ray tube current modulation pattern is changed using an increase rate of the standard deviation based on the amount of displacement calculated from the relationship.

8. The X-ray CT apparatus according to claim 1,
   characterized in that the amount of displacement includes a vertical component and a horizontal component.

9. The X-ray CT apparatus according to claim 1, characterized by further comprising:
   a subject moving unit which moves the subject so that the desired position of the subject matches the rotation center of the X-ray source.

10. An X-ray CT apparatus comprising:
    an X-ray source which emits X-rays while rotating around a subject;

a compensation filter which adjusts at least one of output distribution and spectral distribution of the X-rays emitted from the X-ray source to the subject;

an X-ray detector which is disposed opposite to the X-ray source with the subject interposed therebetween, rotates together with the X-ray source, and detects an amount of X-rays transmitted through the compensation filter and the subject;

an image operation unit which reconstructs a tomographic image of the subject on a basis of the detected amount of X-rays;

a display unit which displays the tomographic image;

a control unit which controls each of the constituent components; and a compensation unit which compensates for deterioration of image quality, which is based on an amount of displacement between a rotation center of the X-ray source and a desired position of the subject, by changing an X-ray tube current modulation pattern indicating a time-series change of emission of the X-rays and/or by moving the position of the subject; and a displacement amount calculating unit which calculates the amount of displacement, which includes a horizontal component, at every slice position.

11. The X-ray CT apparatus according to claim 1, characterized by further comprising:

an ROI setting unit which sets an ROI on a scanogram image; and a subject moving unit which moves the subject so that the center of the ROI corresponds with the rotation center of the X-ray source.

12. An X-ray CT apparatus comprising:

an X-ray source which emits X-rays while rotating around a subject;

a compensation filter which adjusts at least one of output distribution and spectral distribution of the X-rays emitted from the X-ray source to the subject;

an X-ray detector which is disposed opposite to the X-ray source with the subject interposed therebetween, rotates together with the X-ray source, and detects an amount of X-rays transmitted through the compensation filter and the subject;

an image operation unit which reconstructs a tomographic image of the subject on a basis of the detected amount of X-rays;

a display unit which displays the tomographic image;

a control unit which controls each of the constituent components; and a compensation unit which compensates for deterioration of image quality, which is based on an amount of displacement between a rotation center of the X-ray source and a desired position of the subject, by changing an X-ray tube current modulation pattern indicating a time-series change of emission of the X-rays and/or by moving the position of the subject; and a subject moving unit which moves the subject so that the central position of a cross-sectional model of the subject corresponds with the rotation center of the X-ray source at every slice position.

13. An X-ray CT method comprising:

a step (a) of emitting X-rays from an X-ray source while rotating the X-ray source around a subject;

a step (b) of detecting an amount of X-rays transmitted through a compensation filter, which adjusts at least one of output distribution and spectral distribution of the X-rays emitted from the X-ray source to the subject, and the subject by means of an X-ray detector which is disposed opposite to the X-ray source with the subject interposed therebetween and rotates together with the X-ray source;

a step (c) of reconstructing a tomographic image of the subject on a basis of the detected amount of X-ray's by s of an image operation unit;

a step (d) of displaying the tomographic image; and a step (e) of compensating for deterioration of image quality, which is based on an amount of displacement between a rotation center of the X-ray source and a desired position of the subject, by changing an X-ray tube current modulation pattern indicating a time-series change of emission of the X-rays and/or by moving the position of the subject; and a step (f) of storing in a storage unit a relationship between the amount of displacement and the deterioration of the image quality, the relationship having been experimentally acquired in advance, wherein the step (e) compensates for the deterioration of image quality, by referring to the relationship stored in the storage unit in the step (f).

14. The X-ray CT method according to claim 13, characterized by further comprising:

a step of calculating a cross-sectional model of the subject on the basis of scanogram projection data obtained by control of a control unit, wherein the desired position is a central position of the cross-sectional model, and a position for compensating the deterioration of the image quality is the center of the tomographic image of the subject.

15. The X-ray CT method according to claim 14, characterized by further comprising:

a step of calculating an X-ray tube current modulation pattern on the basis of the cross-sectional model.

* * * * *